United States Patent
Centanni

(10) Patent No.: US 6,909,972 B2
(45) Date of Patent: *Jun. 21, 2005

(54) METHOD AND APPARATUS FOR FORMULATING AND CONTROLLING CHEMICAL CONCENTRATIONS IN A SOLUTION

(75) Inventor: Michael A. Centanni, Parma, OH (US)

(73) Assignee: Steris Inc., Temecula, CA (US)

( * ) Notice: Subject to any disclaimer, the term of this patent is extended or adjusted under 35 U.S.C. 154(b) by 44 days.

This patent is subject to a terminal disclaimer.

(21) Appl. No.: 10/456,378

(22) Filed: Jun. 6, 2003

(65) Prior Publication Data

US 2004/0249579 A1 Dec. 9, 2004

(51) Int. Cl.⁷ ............................................. G01R 27/26
(52) U.S. Cl. ............................ 702/25; 702/30; 702/31; 702/32
(58) Field of Search ........................... 702/25, 30–32; 73/24.041, 31.061, 23.2; 422/3, 28, 110, 108, 105, 32, 111, 298, 305, 88; 134/113, 562–582, 18, 26–30

(56) References Cited

U.S. PATENT DOCUMENTS

| | | | |
|---|---|---|---|
| 3,636,444 A | 1/1972 | Strawn et al. | 324/61 R |
| 3,778,706 A | 12/1973 | Thompson | 324/61 R |
| 3,816,811 A | 6/1974 | Cmelik | 324/61 R |
| 4,031,742 A | 6/1977 | Michael et al. | 73/40.7 |
| 4,158,810 A | 6/1979 | Leskovar | 324/127 |
| 4,219,776 A | 8/1980 | Arulanandan | 324/323 |
| 4,427,772 A | 1/1984 | Kodera et al. | 435/27 |
| 4,509,522 A | 4/1985 | Manuccia et al. | 128/634 |
| 4,525,265 A | 6/1985 | Abe et al. | 204/403 |
| 4,674,879 A | 6/1987 | Gregorig et al. | 356/301 |
| 4,857,152 A | 8/1989 | Armstrong et al. | 204/1 T |
| 5,151,660 A | 9/1992 | Powers et al. | 324/689 |
| 5,157,968 A | 10/1992 | Zfira | 73/149 |
| 5,171,523 A | 12/1992 | Williams | 422/20 |
| 5,243,858 A | 9/1993 | Erskine et al. | 73/204.26 |
| 5,364,510 A | 11/1994 | Carpio | 204/153.1 |
| 5,439,569 A | 8/1995 | Carpio | 204/153.1 |
| 5,459,568 A | 10/1995 | Yano et al. | 356/336 |
| 5,470,754 A | 11/1995 | Rounbehler et al. | 436/106 |
| 5,600,142 A | 2/1997 | Van Den Berg et al. | 250/339.13 |
| 5,847,276 A | 12/1998 | Mimken et al. | 73/453 |
| 5,861,303 A | 1/1999 | Barshter et al. | 435/266 |
| 5,882,590 A | 3/1999 | Stewart et al. | 422/28 |

(Continued)

OTHER PUBLICATIONS

U.S. Appl. No. 10/872,227, filed Jun. 18, 2004, Kaiser et al., entitled: Method and Apparatus for Monitoring the Purity and/or Quality of Steam.

(Continued)

Primary Examiner—Carol S. W. Tsai
(74) Attorney, Agent, or Firm—Kusner & Jaffe; Michael A. Centanni

(57) ABSTRACT

A method and apparatus for formulating and controlling concentrations of deactivating chemicals in a solution inside a chamber. The solution may include chemical components that are deactivating chemicals, as well as chemical components that are base chemicals, acting as a diluent for a deactivating chemical, or as a vehicle or carrier for a deactivating chemical. A capacitor is exposed to the solution, wherein the solution comprises a dielectric material between the plates of the capacitor. Permittivity of the dielectric is affected by the relative concentrations of the chemical components, and thus a measurement of the electrical properties of the capacitor can be used to determine the concentration levels of multiple chemical components in the solution.

76 Claims, 3 Drawing Sheets

U.S. PATENT DOCUMENTS

| | | | | |
|---|---|---|---|---|
| 5,997,685 | A | * 12/1999 | Radhamohan et al. | 156/345.1 |
| 6,162,409 | A | * 12/2000 | Skelley et al. | 423/239.1 |
| 6,369,387 | B1 | 4/2002 | Eckles | 250/343 |
| 6,454,874 | B1 | 9/2002 | Jacobs et al. | 134/18 |
| 6,614,242 | B2 | 9/2003 | Matter et al. | 324/698 |
| 6,660,231 | B2 | 12/2003 | Moseley | 422/98 |
| 6,706,648 | B2 | * 3/2004 | Yamazaki et al. | 438/790 |
| 2002/0014410 | A1 | 2/2002 | Silveri et al. | 204/412 |
| 2002/0033186 | A1 | * 3/2002 | Verhaverbeke et al. | 134/26 |
| 2002/0076492 | A1 | * 6/2002 | Loan et al. | 427/255.28 |
| 2002/0109511 | A1 | 8/2002 | Frank | 324/663 |
| 2002/0111040 | A1 | * 8/2002 | Yamazaki et al. | 438/783 |
| 2002/0157686 | A1 | * 10/2002 | Kenny et al. | 134/13 |
| 2003/0063997 | A1 | 4/2003 | Fryer et al. | 422/3 |
| 2003/0102007 | A1 | * 6/2003 | Kaiser | 134/1 |
| 2003/0157587 | A1 | * 8/2003 | Gomez et al. | 435/30 |
| 2004/0029257 | A1 | * 2/2004 | Dutil et al. | 435/266 |
| 2004/0079395 | A1 | * 4/2004 | Kim et al. | 134/30 |
| 2004/0178799 | A1 | 9/2004 | Korenev et al. | 324/453 |
| 2004/0178802 | A1 | * 9/2004 | Centanni | 324/662 |
| 2004/0178803 | A1 | * 9/2004 | Centanni | 324/662 |
| 2004/0178804 | A1 | * 9/2004 | Allen et al. | 324/662 |
| 2004/0262170 | A1 | 12/2004 | Centanni | 205/782 |

OTHER PUBLICATIONS

U.S. Appl. No. 10/896,609, filed Jul. 21, 2004, Kaiser et al., entitled: Method and Apparatus for Real Time Monitoring or Metallic Cation Concentrations in a Solution.

U.S. Appl. No. 10/900,745, filed Jul. 28, 2004, Kaiser et al., entitled: Method and Apparatus for Monitoring the State of a Chemical Solution for Decontamination of Chemical and Biological Warfare Agents.

U.S. Appl. No. 10/931,186, filed Aug. 31, 2004, Kaiser et al., entitled: Method and Apparatus for Monitoring Detergent Concentration in a Decontamination Process.

Philipp, "Charge Transfer Sensing," 1997.

Wojslaw, "Everything You Wanted to Know About Digitally Programmable Potentiometers," Catalyst Semiconductor, Inc., Oct. 17, 2001, Publication No. 6009.

Kittel, "Introduction to Solid State Physics," Fourth Edition, John Wiley & Sons, Inc., 1971.

Philipp, "The Charge Transfer Sensor," Sensors Magazine, Oct. 1999.

U.S. Appl. No. 10/389,036, filed Mar. 14, 2003, Centanni, entitled: Method and Apparatus for Measuring Chemical Concentration in a Fluid.

U.S. Appl. No. 10/405,880, filed Apr. 2, 2003, Centanni, entitled: Method and Apparatus for Measuring Concentration of a Chemical Component in a Gas Mixture.

U.S. Appl. No. 10/456,380, filed Jun. 6, 2003, Centanni, entitled: Method and Apparatus for Formulating and Controlling Chemical Concentrations in a Gas Mixture.

U.S. Appl. No. 10/667,988, filed Sep. 22, 2003, Korenev et al., entitled: Method and Apparatus for Measuring the Concentration of Hydrogen Peroxide in a Fluid.

T. J. Buckley et al., "*Toroidal Cross Capacitor for Measuring the Dielectric Constant of Gases,*" Review of Scientific Instruments, vol. 71, No. 7, Jul. 2000, pp. 2914–2921.

Gross et al., "*The Dielectric Constants of Water Hydrogen Peroxide and Hydrogen Peroxide–Water Mixtures,*" L. Amer. Chem. Soc., vol. 72, 1950, pp. 2075–2080.

"*Humidity Sensor Theory and Behavior,*" Psychometrics and Moisture, Honeywell HVAC, Nov. 27, 2002.

\* cited by examiner

METHOD AND APPARATUS FOR FORMULATING AND CONTROLLING CHEMICAL CONCENTRATIONS IN A SOLUTION

FIELD OF THE INVENTION

The present invention relates to a method and apparatus for formulating and controlling the concentration of chemicals, and more particularly to a method and apparatus for formulating and controlling concentrations of chemical components of a multi-component solution inside a chamber.

BACKGROUND OF THE INVENTION

The degree of polarity of a molecule is expressed in terms of a "dipole moment." Molecules, such as water, that exhibit a separation of charge within the molecule, have non-zero dipole moments. If the separated charges are equal in magnitude but opposite in sign, the magnitude of the dipole moment is equal to the product of the value of one of the separated charges and the distance of separation between the charges. The dipole moment is a vector that points from the negatively charged side of the molecule to the positively charged side of the molecule. The dipole moment depends on three factors, namely, (1) polarity of the molecule, (2) the magnitude of the separated charge, and (3) the geometry of the molecule. It is known that different molecules will have different dipole moments. For instance, molecules of deactivating chemicals, such as ozone ($O_3$), and hydrogen peroxide ($H_2O_2$), have different dipole moments than molecules of water ($H_2O$).

The present invention uses differences in the dipole moments of different molecules as a means for formulating and controlling the concentration of a chemical component in a multi-component solution.

SUMMARY OF THE INVENTION

In accordance with the present invention, there is provided a method for deactivating a contamination inside a chamber, the method comprising: combining a plurality of chemical components in the chamber to form a solution, each chemical component having a respective concentration therein, wherein the respective concentrations of the chemical components are determined by: exposing at least one capacitor, having first and second plates, to the solution, and determining a change in an electrical property of the at least one capacitor, wherein said change in the electrical property varies in accordance with a change in the respective concentrations of the chemical components in the solution.

In accordance with another aspect of the present invention there is a method for deactivating a contamination inside a chamber, the method comprising: selecting at least one contamination to be deactivated in the chamber; and combining a plurality of chemical components in the chamber to form a solution, each chemical component having a respective concentration therein, wherein the concentration of the first and second chemical components are determined by: exposing at least one capacitor, having first and second plates, to the solution, and determining a change in an electrical property of the at least one capacitor, wherein said change in the electrical property varies in accordance with changes in the respective concentrations of at least one of said chemical components.

According to another aspect of the present invention, there is provided a system for deactivating a contamination inside a chamber, the system comprising: means for combining a plurality of chemical components in the chamber to form a solution, each chemical component having a respective concentration therein; means for determining the respective concentrations of the chemical components including: at least one capacitor, having first and second plates exposed to the solution, and means for determining a change in an electrical property of the at least one capacitor, wherein said change in the electrical property varies in accordance with a change in the respective concentrations of the chemical components in the solution.

In accordance with yet another aspect of the present invention, there is provided a system for deactivating a contamination inside a chamber, the system comprising: input means for selecting at least one contamination to be deactivated in the chamber, means for combining a plurality of chemical components in the chamber to form a solution, each chemical component having a respective concentration therein; and means for determining the respective concentrations of the chemical components including: at least one capacitor, having first and second plates exposed to the solution, and means for determining a change in an electrical property of the at least one capacitor, wherein said change in the electrical property varies in accordance with a change in the respective concentrations of the chemical components in the solution.

In accordance with still another aspect of the present invention, there is provided a method of controlling the concentration of a plurality of chemical components of a solution in a chamber, the method comprising: storing a plurality of data sets in a memory, each data set respectively indicative of decay of a chemical component, wherein each data set includes values of an electrical property of a capacitor associated with chemical component concentrations as a function of time; and replenishing the concentration of at least one of the chemical components after an operating time period in accordance with the plurality of data sets.

According to still another aspect of the present invention, there is provided a method of controlling concentration of a chemical component of a solution in a chamber, the method comprising: developing an equation defining an electrical property of a capacitor associated with concentration of a chemical component as a function of time; and replenishing the concentration of the chemical component after an operating time period in accordance with said equation.

An advantage of the present invention is the provision of a method and apparatus for formulating and controlling chemical concentrations that senses the concentrations using electrical properties of a capacitor.

Still another advantage of the present invention is the provision of a method and apparatus for formulating and controlling chemical concentrations that are simple and inexpensive to implement.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF A PREFERRED EMBODIMENT

It should be understood that the term "solution," as used herein, refers to a homogenous system of two or more substances, including mixtures of multiple liquids, mixtures of one liquid and a single gas or multiple gases, or mixtures of multiple liquids and a single gas or multiple gases. Moreover, while a preferred embodiment of the present invention is described herein with particular reference to deactivation of biocontamination, it is contemplated that the invention may also be used in deactivation of other types of contamination not specifically identified herein.

Figure 1:
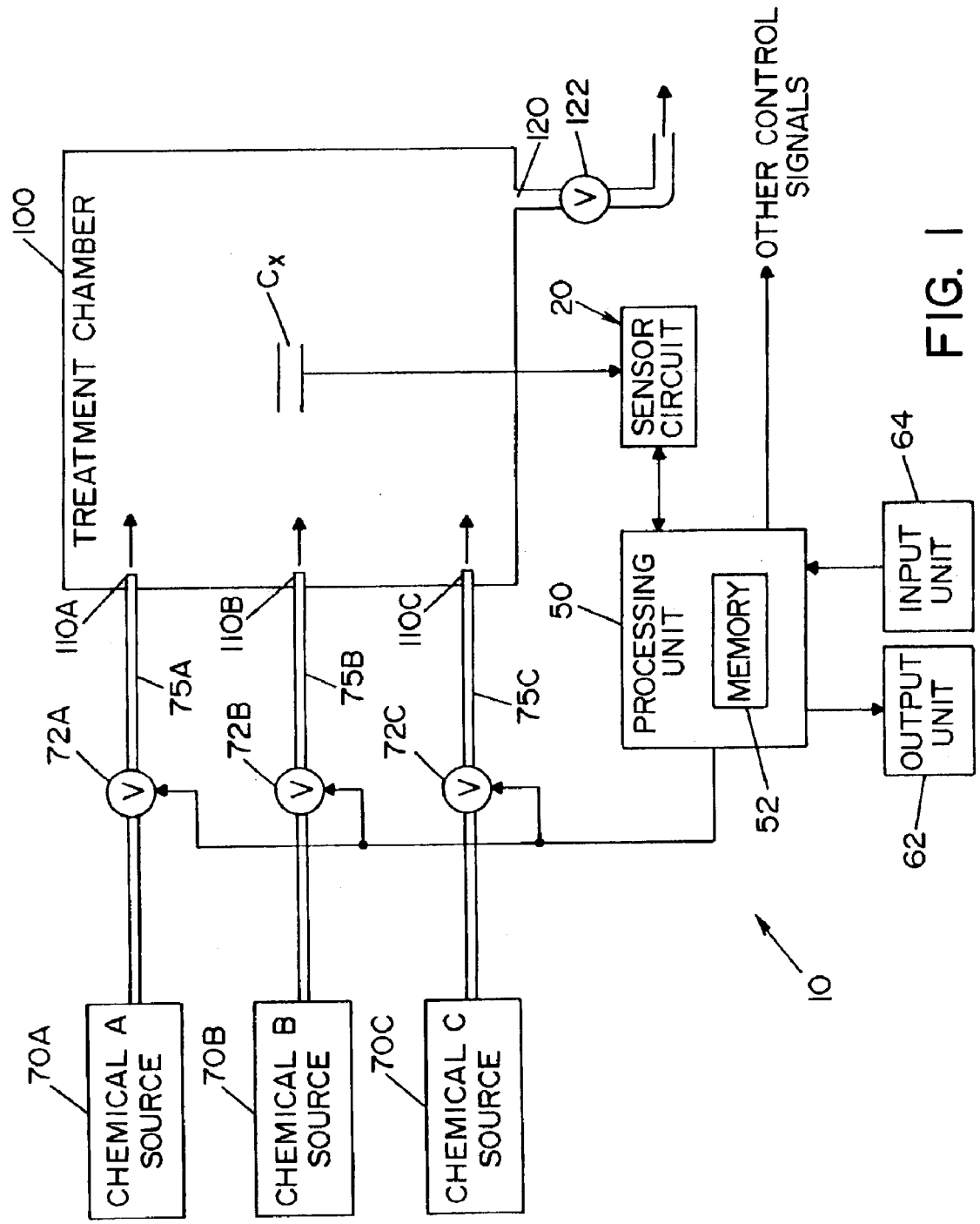
FIG. 1 is a block diagram of a chemical concentration formulating and controlling system, according to a preferred embodiment of the present invention.

Referring now to the drawings wherein the showings are for the purposes of illustrating a preferred embodiment of the invention only and not for purposes of limiting same, FIG. 1 shows a contamination deactivating system 10, according to a preferred embodiment of the present invention. System 10 includes chemical sources 70A–70C, valves 72A–72C, conduits 75A–75C, a treatment chamber 100, and a chemical concentration formulating and controlling system. Chemical sources 70A–70C respectively provide a source of chemicals A, B and C. Conduits 75A–75C respectively provide a travel path for chemicals A, B and C to enter chamber 100. Valves 72A–72C are movable between open and closed positions to respectively control the flow of chemicals A, B and C into conduits 75A–75C.

It should be understood that chemicals A, B and C may include "deactivating chemicals" (including, but not limited to antimicrobial chemicals), as well as "base chemicals" and "pre-treatment chemicals." Base chemicals act as a diluent for a deactivating chemical, or as a vehicle or a carrier for a deactivating chemical. The base chemical may itself be a deactivating chemical or have deactivating properties. Pre-treatment chemicals include chemicals that make a biocontamination more susceptible to deactivation by a deactivating chemical. In the case of prions, pre-treatment chemicals may operate to change a conformational state of the prions, making the prions more susceptible to deactivation. It should be further appreciated that while a preferred embodiment of the present invention is described with reference to a system 10 using three chemicals A, B and C, the number of chemicals used for contamination deactivation may be greater or less than three.

Chamber 100 provides a region wherein articles, devices, apparatus, and other objects are exposed to a plurality of deactivating chemicals to effect deactivation of biocontamination (e.g., decontamination or sterilization). In the illustrated embodiment, chamber 100 is an enclosed region suitable for containing liquids and gases. Chamber 100 includes input ports 110A–110C and an output port 120. Input ports 110A–110C are in communication with conduits 75A–75C Output port 120 provides access to an exit path, to allow fluid inside chamber 100 to exit therefrom. A valve 122 is movable between an open position and a closed position. In the open position, fluid inside chamber 100 exits chamber 100. The volume of chamber 100 may typically range from less than 1 cubic foot to about 15 cubic feet. Fluid exiting chamber 100 may be filtered, recirculated back into chamber 100, or exit to a drain.

Chemical concentration formulating and controlling system is generally comprised of a sensor circuit 20, a processing unit 50, an output unit 62, and an input unit 64. Sensor circuit 20 includes a capacitor $C_x$ to sense a concentration of chemical components in a solution inside chamber 100, as will be described in detail below. It should be appreciated that the chemical concentration formulating and controlling system may include a plurality of sensor circuits 20 in order to sense a concentration of chemical components in more than one region of chamber 100.

According to a preferred embodiment, the solution inside chamber 100 may include (but is not limited to) chemical components that are deactivating chemicals for biocontamination deactivation, such as antimicrobial chemicals (e.g., decontaminants and sterilants), and "base" chemicals. It is contemplated by the inventor that the solution may include chemical components not specifically identified herein, as well as chemical components unrelated to a biocontamination deactivation process, including chemicals having different dipole moments.

In a preferred embodiment, processing unit 50 operates with sensor circuit 20, and outputs control signals to valves 72A–72C to move valves 72A–72C between the open and closed position. In addition, processing unit 50 may also output other control signals for the operation of other system elements, such as control means (not shown) for controlling the production of a gas (e.g., a vaporization system) at sources 70A–70C. Processing unit 50 may also output signals to an output unit 62 to provide operator information in an audible and/or visual form. Accordingly, output unit 62 may take the form of an audio speaker and/or visual display unit. Input unit 64 provides a means for entering information into processing unit 50. In this regard, input unit 64 may take the form a keyboard, keypad, switches, and the like. In a preferred embodiment, processing unit 50 takes the form of a microcomputer or microcontroller, including a memory 52 for data storage.

Figure 2:
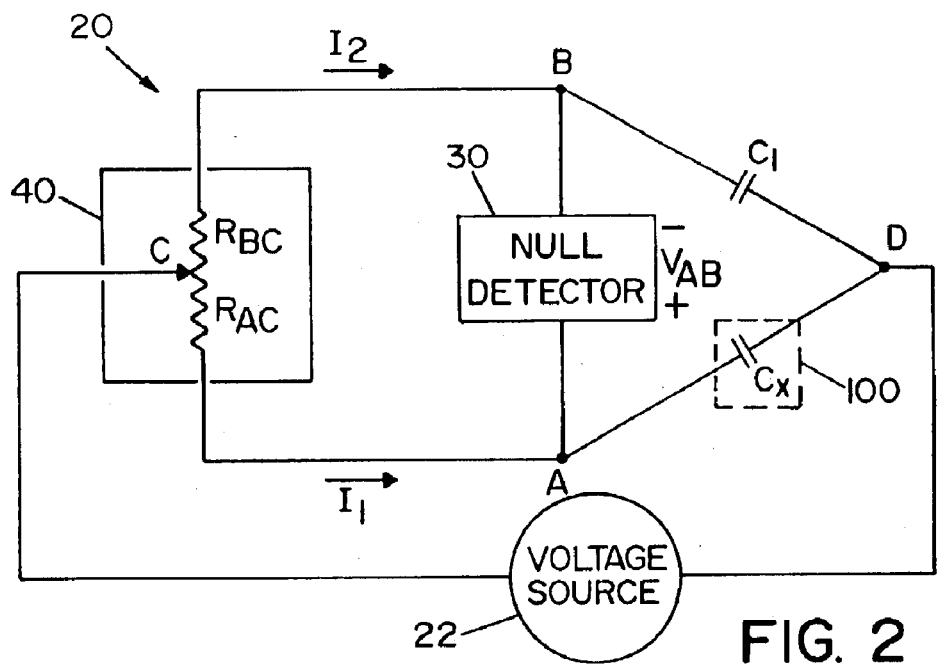
FIG. 2 is a schematic diagram illustrating a sensor circuit.

Referring now to FIG. 2, there is shown a detailed schematic of an exemplary sensing circuit 20. Sensor circuit 20 takes the form of a "bridge circuit." As is well known to those skilled in the art, bridge circuits are used to determine the value of an unknown impedance in terms of other impedances of known value. Highly accurate measurements are possible because a null condition is used to determine the unknown impedance. The bridge circuit is used to determine a capacitance value indicative of the concentrations of chemical components in chamber 100. In the embodiment shown in FIG. 2, sensing circuit 20 is generally comprised of a voltage source 22, a null detector 30, an electronic potentiometer 40, a capacitor $C_1$ of known capacitance, and a capacitor $C_x$. Capacitor $C_1$ is a conventional capacitor located outside chamber 100, or is insulated from the solution inside chamber 100.

Capacitor $C_x$ is directly exposed to a solution inside chamber 100, wherein the solution fills the gap between the conducting plates of capacitor $C_x$, thereby acting as an insulator or "dielectric" of capacitor $C_x$. Sensor circuit 20 provides data indicative of a capacitance $C_x$, corresponding to a chemical concentration. In this regard, capacitance $C_x$ will vary in accordance with changes in the concentration of chemical components inside chamber 100.

It should be appreciated that the solution may not be the sole dielectric in the gap between the conducting plates of capacitor $C_x$. In this regard, it is contemplated that one or more solid dielectric materials may also be present in the gap, including, but not limited to, organic or inorganic materials.

In a preferred embodiment, capacitor $C_x$ is a parallel plate capacitor. However, it should be appreciated that capacitor $C_x$ could be constructed in a different form. For example, $C_x$ could be a cylindrical or spherical capacitor. If a spherical capacitor is used as capacitor $C_x$, holes must be placed in the outer shell of the capacitor such that the solution can enter and exit the capacitor.

Electronic potentiometer 40 functions in the same manner as a mechanical potentiometer. In this regard, electronic potentiometer 40 is a three terminal device. Between two of the terminals is a resistive element. The third terminal known as the "wiper" is connected to various points along the resistive element. The wiper is digitally controlled by processing unit 50 (see FIG. 1). The wiper divides the resistive element into two resistors $R_{BC}$ and $R_{AC}$. Electronic potentiometer 40 may take the form of a digitally programmable potentiometer (DPP™) available from Catalyst Semiconductor, Inc. of Sunnyvale, Calif.

In a preferred embodiment, voltage source 22 provides an AC voltage signal, such as a sinusoidal or pulse waveform. Null detector 30 is a device for detecting a null condition (i.e., a short circuit), such as a galvanometer, a voltmeter, a frequency-selective amplifier, and the like.

Operation of sensor circuit 20 will now be described in detail. The elements of the bridge circuit are connected between junctions AC, BC, AD, and BD. Electronic potentiometer 40 is operated by processing unit 50 to vary the resistances $R_{BC}$ and $R_{AC}$ until the potential difference between junctions A and B ($V_{AB}$) is zero. When this situation exists, the bridge is said to be balanced or is "nulled." The following relationships then hold for voltages in the main branches:

$$V_{AC}=V_{BC}, \text{ and } V_{AD}=V_{BD},$$

where $V_{AC}$ is the voltage between junctions A and C, $V_{BC}$ is the voltage between junctions B and C, $V_{AD}$ is the voltage between junctions A and D, and $V_{BD}$ is the voltage between junctions B and D. Accordingly, $$V_{AD}/V_{AC}=V_{BD}/V_{BC}$$

$$V_{AD}=V_{BD}/(V_{AC}/V_{BC})$$

The capacitance of capacitor $C_x$ is connected between junctions A and D with a known capacitance of capacitor $C_1$ between junctions B and D. Electronic potentiometer 40, connected from junction A to junction C to junction B, is adjusted by processing unit 50 to vary the voltages $V_{AC}$ and $V_{BC}$.

When a null is detected by null detector 30, current $I_1$ flows from junction C to junction A to junction D, and a current $I_2$ flows from junction C to junction B to junction D. The voltage $V_{AC}$ across junctions A to C, and the voltage $V_{BC}$ across junctions B to C are:

$$V_{AC}=I_1 R_{AC} \text{ and } V_{BC}=I_2 R_{BC}.$$

The voltage across a capacitor with capacitance C, current I, and frequency f is:

$$V = \frac{I}{2\pi f C}$$

Therefore, the voltages $V_{AD}$ and $V_{BD}$ may be expressed as:

$$V_{AD} = \frac{I_1}{2\pi f C_x}$$

$$V_{BD} = \frac{I_2}{2\pi f C_1}$$

As discussed above, $V_{AD}=V_{BD}/(V_{AC}/V_{BC})$, $V_{AC}=I_1 R_{AC}$, and $V_{BC}=I_2 R_{BC}$. Therefore, $$C_x = C_1 \left( \frac{R_{BC}}{R_{AC}} \right).$$

In view of the forgoing relationship, when a null condition is detected, the resistance values for $R_{BC}$ and $R_{AC}$, along with the known capacitance value of capacitor $C_1$, can be used to determine unknown value of capacitance for capacitor $C_x$.

Differences in dipole moments of different molecules are used to determine the concentration of chemical components in a solution. In this regard, the dielectric constant of a capacitor is dependent on electronic "polarizability." Polarization is the ability of molecules to form a dipole under an electric field or the ability of the electric field to line up or rotate an inherent dipole, such as water molecules. In the event there is only one chemical component in the solution that has a measurable dipole moment, the concentration of that chemical component is determined.

As discussed above, the solution fills the gap between the conducting plates of capacitor $C_x$, thereby acting as a dielectric of capacitor $C_x$. By configuring capacitor $C_x$ as an element of a bridge circuit, a measure of resistance values $R_{AC}$ and $R_{BC}$, when the bridge is balanced or nulled, can be used to determine the capacitance of capacitor $C_x$. The capacitance of capacitor $C_x$ is indicative of concentrations of chemical components in chamber 100, since the permittivity of the respective dielectric is affected by the concentrations of the chemical components in the solution.

It is well known that for a parallel plate capacitor $C=(\kappa \epsilon_0)(A/d)=(\epsilon)(A/d)$, where C is capacitance, $\kappa$ is the dielectric constant, $\epsilon_0$ is the permittivity of free space (8.85×10$^{-12}$ F/m), $\epsilon$ is the permittivity (Farads/meter) of the capacitor dielectric, A is the area of the capacitor plates (m$^2$), and d is the separation in meters between the capacitor plates. As $\epsilon$ increases, the capacitance C will increase. Where the capacitor is a parallel plate capacitor with circular plates of diameter D, $C=(\pi D^2 \epsilon)/(4d)$.

It will be appreciated that the dielectric constant $\kappa$ of the capacitor can be determined according to the following expression:

$$\kappa = \frac{4dC}{\pi D^2 \epsilon_0},$$

where the value of capacitance, C, is determined as discussed above. The dielectric constant ($\kappa$) of the capacitor can also be determined by determining the capacitance with the dielectric in place between the conducting plates ($C_d$), and then determine the capacitance without the dielectric in place ($C_o$). The ratio of the two capacitances equals the dielectric constant, $$\kappa = \frac{C_d}{C_0}.$$

The response of a capacitor is influenced by the characteristics (e.g., frequency) of the AC waveform applied thereto. In this regard, capacitive reactance ($X_c$) is a function of frequency. Capacitive reactance is the opposition offered to the flow of alternating current by pure capacitance, and is expressed in ohms ($X_c = 1/(2\pi f C)$). Accordingly, frequency of the waveform generated by voltage source 22 influences the response of capacitors. Thus, the frequency selected for voltage source 22 should preferably be a frequency that will provide a generally linear response for capacitance as the concentration of a chemical component inside chamber 100 is varied. This will facilitate the use of interpolation and extrapolation of capacitance values, as will be discussed further below. If a suitable linear response is not obtained, then an expanded set of data points may be stored in memory 52.

Figure 3:
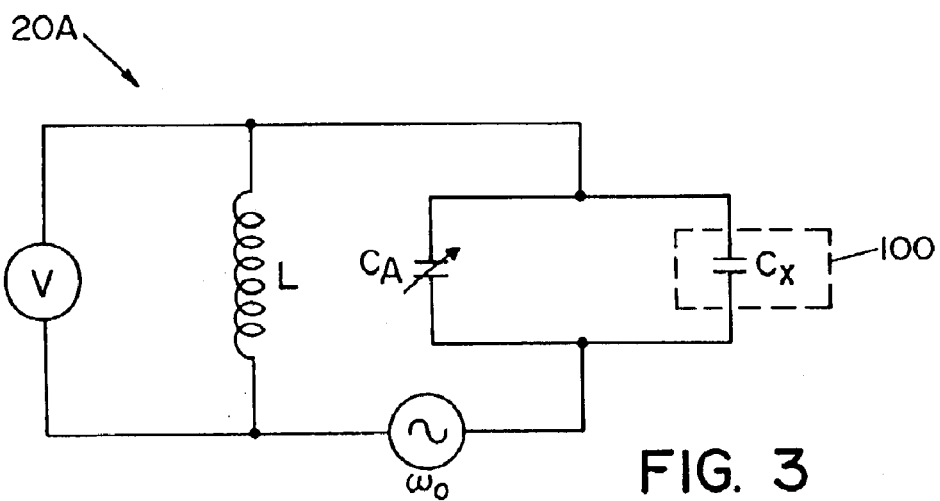
FIG. 3 is a schematic diagram illustrating a first alternative sensor circuit.

It should be appreciated that while one embodiment of the present invention includes a sensor circuit 20 in the form of a bridge circuit, other types of circuits and techniques (including other types of bridge circuits, and capacitance meters) known to those skilled in the art, are suitably used to measure capacitance. For example, FIG. 3 illustrates an alternative sensor circuit 20A. Sensor circuit 20A is an LC resonant circuit, having a variable capacitor $C_A$ located outside chamber 100 (or otherwise isolated from the solution inside chamber 100), and a capacitor $C_x$ directly exposed to the solution. In this regard, capacitor $C_x$ is located in chamber 100, wherein the solution fills the gap between the conducting plates of capacitor $C_x$, thereby acting as an insulator or "dielectric" of capacitor $C_x$. Since the resonance frequency $\omega_0 = [L(C_A + C_x)]^{-1/2}$, the unknown capacitance of capacitor $C_x$ can be determined.

Figure 4:
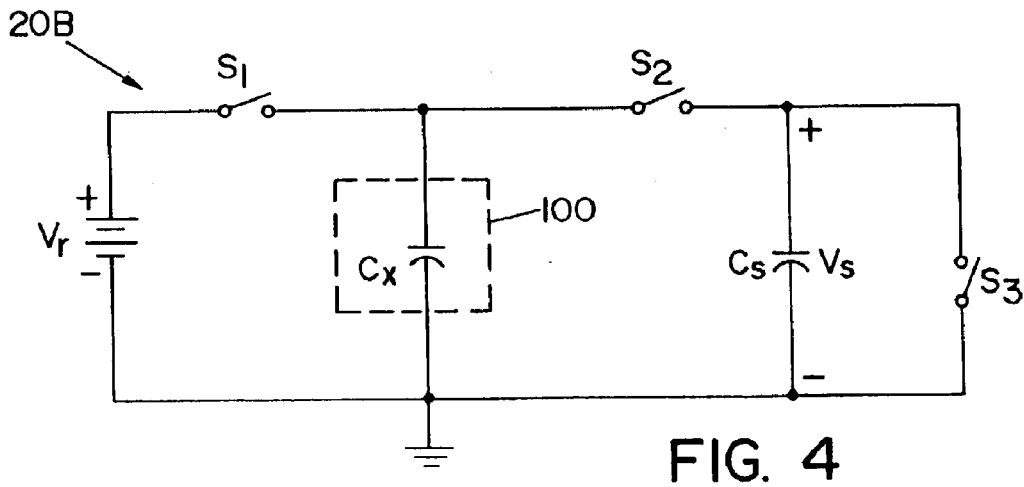
FIG. 4 is a schematic diagram illustrating a second alternative sensor circuit.

FIG. 4 illustrates yet another alternative sensor circuit 20B suitable for use in connection with the present invention. Sensor circuit 20B is a "charge transfer" sensor circuit. Charge transfer sensor circuits are recognized to provide resolutions of fractions of a femtoFarad. In a charge transfer sensor circuit the unknown capacitance of a sense electrode is determined by charging the sense electrode to a fixed potential, and then transferring that charge to a charge detector comprising a capacitor of known capacitance. In sensor circuit 20B, capacitor $C_x$ of unknown capacitance is located in chamber 100, wherein the solution fills the gap between the conducting plates of capacitor $C_x$, thereby acting as an insulator or "dielectric" of capacitor $C_x$. Capacitor $C_x$ is first connected to a DC reference voltage ($V_r$) via a switch $S_1$. Switch $S_1$ is reopened after $C_x$ is satisfactorily charged to the potential of $V_r$. Then, after as brief as possible a delay so as to minimize leakage effects caused by conductance, switch $S_2$ is closed, and the charge (Q) present on $C_x$ is transferred to capacitor $C_s$ (i.e., the charge detector). Once the charge Q is satisfactorily transferred to capacitor $C_s$, switch $S_2$ is reopened. By reading voltage $V_s$, the capacitance of capacitor $C_x$ can be determined. $V_s$ may be input to an amplifier to provide the scaling necessary to present an analog-to-digital converter (ADC) with a useful range of voltage for digital processing. Switch $S_3$ acts as a reset means to reset the charge between charge transfer cycles, so that each charge transfer cycle has a consistent initial condition. Switches $S_1$, $S_2$ and $S_3$ may be electromechanical switches or transistors. Preferably, digital control logic is used to control switches $S_1$, $S_2$ and $S_3$. In a preferred embodiment, CS is selected to be significantly larger that $C_x$.

The equations governing sensor circuit 20B are as follows:

$V_s = V_r [C_x/(C_x + C_s)]$, therefore $C_x = V_s C_s/[V_r - V_s]$.

It is recognized that in some cases, the capacitance of the capacitor exposed to the solution located in chamber 100 may be in the range of sub-femtoFarad capacitance to low picoFarad capacitance (e.g., 0.1 fF to 100 pF), and that changes in concentration of chemical components in the solution may only result in a change of capacitance in the range of low picoFarad capacitance or even femtoFarad capacitances. Accordingly, the sensor circuit used to measure capacitance may need to have high sensitivity to allow for measurement of small values of capacitance. One high sensitivity sensor circuit is the charge transfer sensor circuit described above. Other high sensitivity circuitry is provided by such devices as the PTL 110 capacitance transducer from Process Tomography Limited of Cheshire, United Kingdom. The PTL 110 measures small values of capacitance (up to 10 picoFarads) with a resolution of 1 femtoFarad. A 1616 Precision Capacitance Bridge from IET Labs, Inc. of Westbury, N.Y., allows for measurement of capacitances in the range from $10^{-7}$ pF to 10 $\mu$F. Tektronix produces the Tektronix 130 LC Meter that measures capacitance from 0.3 pF to 3 pF. It has also been acknowledged in the prior art literature that capacitance sensor circuits using modern operational amplifiers and analog-to-digital converters (ADCs) can easily obtain resolutions to 0.01 pF.

It should be appreciated that while a preferred embodiment of the present invention uses a measure of a capacitor's capacitance to determine concentrations, it is also contemplated that a measure of other electrical properties of a capacitor may be used to determine concentrations, including, but not limited to, voltage, current, resistance, reactance, charge, permittivity, dielectric constant, or a change in any other electrical property.

Figure 5:
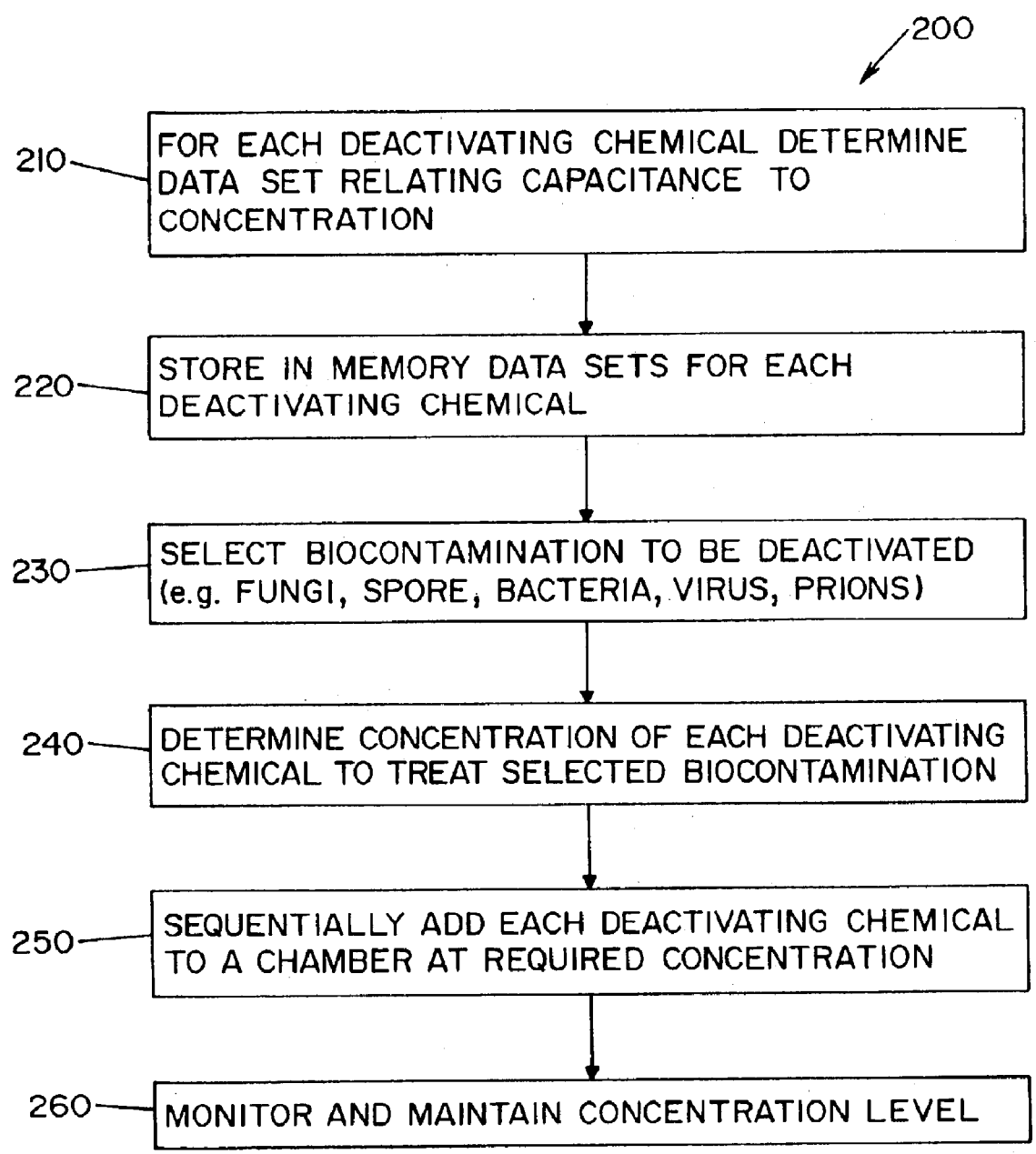
FIG. 5 is a flow diagram illustrating a method for formulating and controlling chemical concentrations of a solution in a chamber.

With reference to FIGS. 1 and 5, operation of a preferred embodiment of the chemical concentration formulating and controlling system, will now be described in detail. FIG. 5 provides a flow diagram 200 describing the formulation and control processes. As indicated above, in the embodiment shown in FIG. 1, chamber 100 is an enclosed region suitable for containing liquids and gases. Chemicals enter input chamber through input ports 110A–110C, and exit chamber 100 through output port 120.

As an initial step, a data set (i.e., table of data representative of a graph of capacitance versus concentration), relating capacitance of capacitor $C_x$ to concentration, is determined for each deactivating chemical of interest (step 210), and stored in memory 52 (step 220). In this regard, chamber 100 is filled with a solution comprised of a first deactivating chemical (e.g., peracetic acid) and a first base chemical (e.g., water), and the capacitance of capacitor $C_x$ is measured as a function of concentration, as the concentrations of the deactivating chemical and base chemical are varied. Capacitor $C_x$ is exposed to the solution comprised of verified concentrations of a first deactivating chemical and verified concentrations of a base chemical to determine a data set associated with the first deactivating chemical. For example, the collected capacitance data may include the capacitance of capacitor $C_x$ determined for the following concentrations of peracetic acid (first deactivating chemical) and water (first base chemical):

0% peracetic acid and 100% water,
25% peracetic acid and 75% water,
50% peracetic acid and 50% water,
75% peracetic acid and 25% water, and
100% peracetic acid and 0% water.

Chamber 100 is then emptied, and filled with a solution comprised of a second deactivating chemical (e.g., ozone) and a second base chemical (e.g., a carrier chemical for ozone). Capacitor $C_x$ is exposed to verified concentrations of a second deactivating chemical (e.g., ozone) and a second base chemical to determine a data set associated with the second deactivating chemical. The forgoing steps are repeated to obtain additional data sets for other deactivating chemicals, base chemicals, and pretreatment chemicals.

It should be appreciated that the concentrations of the chemical components may be verified using well known analytical tools. The analytic tool is preferably selected in accordance with concentration ranges, size of region, desired response time, and duration of measurement. Examples of well known analytic tools for measuring concentrations of chemical components include, but are not limited to, titration and various forms of spectroscopy.

After the data sets are stored in memory 52 for each chemical component of interest, processing unit 50 can commence "formulation" operations. With reference to step 230 (FIG. 5), a user selects one or more contaminations to be treated using input unit 64 (e.g., spores, fungi, viruses, bacteria, prions, and other biocontaminants). Processing unit 50 then determines a proper formulation of deactivating chemicals for deactivation of the one or more selected contaminants (step 240). In this regard, processing unit 50 is pre-programmed with data for determining appropriate concentrations of a blend of chemical components to effect proper deactivation of the selected contamination(s). For example, if spores are selected as the contamination, a blend of deactivating chemicals most effective at deactivating spores is determined (e.g., X ppm of a first deactivating chemical and Y ppm of a second deactivating chemical). It is contemplated that processing unit 50 is programmed to recognize a hierarchy of contaminants, wherein some contaminants are more difficult to deactivate than others (e.g., prions). Accordingly, processing unit 50 may determine a deactivation chemistry for deactivating a more difficult to deactivate contamination, that would likewise be effective to deactivate less difficult to deactivate contaminants. For example, a deactivation chemistry effective to deactivate prions might also be effective to deactivate spores and bacteria. Therefore, processing unit 50 is programmed to determine an optimum deactivation chemistry for deactivating a plurality of selected contaminants.

After processing unit 50 has determined the concentrations of each chemical component in the blend of deactivating chemicals, each chemical component is sequentially added to chamber 100 in their respective concentrations to form a solution of combined deactivating chemicals (step 250). For example, if the determined blend of deactivating chemicals is comprised of X ppm of chemical A (e.g., ozone) and Y ppm of chemical B (e.g., chlorine dioxide), processing unit will maintain valves 72B and 72C in a closed position, and open valve 72A to release chemical A into chamber 100. The concentration of chemical A is determined using sensor circuit 20 and the pre-stored data sets. If the capacitance of capacitor $C_x$ is not found in the pre-stored data, the stored data may be interpolated or extrapolated to obtain a concentration corresponding to the measure capacitance of capacitor $C_x$.

When the desired concentration level of X ppm of chemical A is sensed by sensor circuit 20, valve 72A is closed.

Next, processing unit 50 opens valve 72B to release chemical B into chamber 100. The concentration of chemical B is increased inside chamber 100 until sensor circuit 20 indicates a capacitance value equal to the sum of: (1) the capacitance value corresponding to X ppm of chemical A and (2) the capacitance value of Y ppm of chemical B, where the capacitance values of (1) and (2) have been pre-stored in memory 52, as discussed above in connection with step 220. In this regard, processing unit 50 uses the total capacitance (i.e., the sum of the capacitance values of (1) and (2)) sensed by sensor circuit 20 to monitor the concentration level of chemical B in chamber 100. When the concentration level of chemical B reaches Y ppm in chamber 100, valve 72B is closed.

For better sensitivity, two or more capacitors may also be connected in parallel in sensor circuit 20. It is also believed that each data set representative of a curve of capacitance versus concentration for fluids of different dipole moments, will have different slopes.

For single polar fluids and mixtures of polar fluids, there exists a dipole-dipole interaction between the molecules of the fluids. In the case of a mixture of two polar fluids, it is believed that this dipole-dipole interaction is inherent in the data taken, i.e., in the collected capacitance versus concentration data. In the case of a mixture of three or more different polar fluids, the dipole-dipole interaction is not inherent in the collected data, unless the capacitance versus concentration were measured for the mixture of polar fluids (e.g., peracetic acid, water, and ozone).

It is believed, however, that in a mixture of fluids where the dipole-dipole interaction between fluids is not inherent in the collected data (e.g., water, peracetic acid and ozone), the dipole-dipole interaction may be neglected for the following reasons. Namely, the force of the dipole-dipole interaction depends on a constant (i.e., 3) times the product of each dipole moment divided by the distance separating the different dipole moments to the fourth power times an orientational quantity composed of the product of cosines and sines of various angles. Simply stated:

$$F \propto p_1 p_2 (\text{orientational factor})/r^4.$$

Since the dipole-dipole force drops off as $r^{-4}$, the different dipoles need to get very close together to affect one another. Given this relationship, the fact that the fluid molecules are moving rapidly and continually bump into each other, and that the chemical component molecules are somewhat dilute, it is believed that the effect of the dipole-dipole interactions on the capacitance versus concentration curves may be neglected. However, it is understood that this interaction does exist so that when three or more different polar fluid molecules are mixed together to form a deactivating fluid, the treatment of the fluids as separate, non-interacting fluids is an approximation. However, as indicated hereinabove, it is believed that the effect that the dipole-dipole interaction between different polar fluids of a solution has on the capacitance versus concentration curves can be neglected, and that the fluids can be treated as "non-interacting," without deviating from the spirit of the present invention.

Referring now to step 260, processing unit 50 continues to monitor the capacitance value sensed by sensor circuit 20, in order to maintain the concentration level in chamber 100 at the desired level, for an appropriate time period. In this regard, processing unit 50 is programmed with the proper exposure time periods to properly deactivate a contamination associated with the articles or devices inside chamber 100.

It should be understood that the temperature at which the data sets are determined at step 210 should generally be the same temperature used during deactivation processing steps 250 and 260.

Processing unit 50 may also be programmed to output other signals, such as control signals for controlling the production of a gas (e.g., an ozone generation process). Processing unit 50 may also output signals to output unit 62 to provide an audible and/or visual indicator when the desired concentrations are not within an acceptable range, and when a deactivation process is complete. The visual indicator may assist an operator by including a display of concentration levels.

As indicated above, the response of a capacitor is influenced by the characteristics (e.g., frequency) of the AC waveform applied thereto. Therefore, frequency of the AC waveform applied to capacitor $C_x$ should be the same throughout steps 210–260.

Furthermore, capacitance values corresponding to various concentrations of different chemicals are believed to be additive, as discussed above. However, it should be appreciated that the capacitance values associated with the concentration of two or more chemical components combined in a solution may also be determined by measuring the capacitance of capacitor $C_x$ as the concentrations of the chemical components are varied. In this regard, capacitor $C_x$ is exposed to a solution comprised of two or more chemical components. The capacitance of capacitor $C_x$ is determined as a function of the concentration of the chemical components, as the concentration of each of the chemical components is varied. In this manner, a large set of data is collected and pre-stored in memory 52 that relates capacitance of capacitor $C_x$ to several different combinations of concentrations of the two or more chemical components. When the concentrations of the chemical components are being formulated, processing unit 50 accesses the pre-stored data to determine the concentrations of the two or more chemical components in the solution.

Many deactivating chemicals decay over time due to chemical activity and environmental conditions (e.g., thermal and photo degradation). For example, ozone is known to rapidly degrade as the ozone molecule ($O_3$) decomposes into molecular oxygen ($O_2$), and peracetic acid in water is subject to hydrolysis and disproportionation. Consequently, it has been observed in deactivation systems that the concentration of chemical components used in the system will decrease over the course of a deactivation processing cycle as a result of decay. In accordance with the present invention, as data sets (i.e., table of data representative of a time decay graph of capacitance versus concentration), relating capacitance of capacitor $C_x$ to concentration, are determined for each deactivating chemical of interest (step 210), additional data sets are acquired that relate capacitance of capacitor $C_x$ as a function of time (i.e., time decay data sets), for each deactivating chemical of interest. In this respect, data is acquired that is indicative of changes in the concentration of the deactivating chemical due to decay.

While the process for monitoring the decay of deactivating chemicals is described herein with reference to sensing a change (e.g., a decrease or an increase) in capacitance, it should be appreciated that the process for monitoring the decay of deactivating chemicals may alternatively be carried out by sensing a change in voltage, current, resistance, reactance, charge, permittivity, dielectric constant, or a change in any other electrical property of the capacitor(s).

In the case of a plurality of deactivating chemicals, the capacitance values for each time decay data set can be summed to determine a data set representative of a time decay graph or curve of total capacitance (i.e., the sum of the capacitance contributed by all of the deactivating chemicals) as a function of time.

As a deactivation process proceeds, the loss in concentration of each deactivating chemical can be determined with reference to the time decay data sets. For example, if there are two deactivating chemicals A and B in chamber 100 during a deactivation process, when an operating time period elapses, decay of each deactivating chemical will contribute to a decrease in the total capacitance measured by sensor circuit 20. It should be understood that the present invention may also be used to monitor decay where only one deactivating chemical is used.

The operating time period may be established by selecting a predetermined time interval, sensing a decrease in total capacitance as established by the decay of deactivating chemicals A and B below a threshold value, or sensing a predetermined percentage decrease in total capacitance. It should be appreciated that the time decay data sets, i.e., of each deactivating chemical, also provide an indication of the rate at which each deactivating chemical decays. This decay rate data can be used for various purposes, including, but not limited to, selecting an appropriate predetermined time interval, threshold value, or percentage decrease.

To replenish both deactivating chemicals A and B to full concentration levels, reference is made to the time decay data sets relating capacitance as a function of time for each deactivating chemical. These time decay data sets provide a means for determining how much of the decrease in total capacitance is attributable to the decay of each of the deactivating chemicals A and B, during the operating time period. Accordingly, the concentration of each of the deactivating chemicals A and B can then be increased an appropriate amount, thus returning each of the deactivating chemicals A and B to their original concentrations. The capacitance values of the time decay data sets can be related to a specific concentration value using the capacitance versus concentration data sets discussed above. Each deactivating chemical is thus replenished until the loss in capacitance for a given time interval, as determined by referencing the individual capacitance versus time curves for each of the deactivating chemicals, is regained.

It should be understood that in cases where the concentration of a first deactivating chemical decreases more rapidly than a second deactivating chemical, just the first deactivating chemical may need to be replenished when a first operating time interval has elapsed. When a second operating time interval has elapsed it may then be necessary to replenish both the first and second deactivating chemical.

If there are no time decay data sets stored for one or more of the specific concentrations of deactivating chemicals used in an actual deactivation process, but data are stored for other concentrations of the same deactivating chemicals, the available stored data can be interpolated to generate suitable time decay data sets for each concentration of the deactivating chemicals actually used. Furthermore, data obtained during a deactivation process may also be added to the stored data so that future deactivation processes using the same chemistries can be more accurately controlled.

It should be understood that historical data may be used to develop equations wherein an electrical property of a capacitor is expressed as a function of time (e.g., capacitance=f(t)). Likewise, equations may be developed wherein a change in an electrical property of a capacitor is expressed as a function of a change in time (e.g., $\Delta$capacitance=f($\Delta$t)). For example, one can measure a portion of the time decay curve of an electrical property of a capacitor for a specific deactivating chemical. Once this portion of data has been taken, conventional curve fitting methods can be used to develop an equation that relates the change in an electrical property of the capacitor as a function of time. Since each value of the electrical property of the capacitor corresponds to a unique concentration of the deactivating chemical, the stored equation would provide values of the electrical properties of the capacitor that correspond to a range of concentrations of the deactivating chemical extending from concentrations of 0% to 100%. Thus, the entire time decay data set is contained in one equation. Typical curve fitting or regression analyses may be used. For example, the method of least squares may be used to provide an equation that corresponds to the portion of data taken. The method of least squares assumes that the best-fit curve of a given type is the curve that has the minimum sum of the deviations squared (least square error) from a given set of data. If, for instance, during an actual deactivation processing cycle the initial concentration of a deactivating chemical corresponds to a measured electrical property of the capacitor equal to X and if a time interval of T has passed since the inception of the run, the system would use the stored equation to determine the value of the electrical property after time interval T has passed. The deactivating chemical would be replenished until the original electrical property X of the capacitor was restored. In addition, as mentioned above, the time derivative of this equation could be taken thus providing an equation that relates a change in an electrical property of the capacitor to a change in time.

As indicated above, there may be more than one sensor circuit 20, each sensor circuit 20 having one or more capacitors for sensing concentration.

While the operation of a preferred embodiment of the present invention has been described with reference to chemical components (e.g., chemicals A, B, and C) that are deactivating chemicals, it should be appreciated that chemical components introduced into chamber 100 may include, but are not limited to, deactivating chemicals (e.g., antimicrobials), base chemicals (i.e., diluents for an deactivating chemical, or vehicles or carriers for a deactivating chemical), pre-treatment chemicals, and combinations thereof. For example, chemical A may be a pre-treatment chemical and chemicals B and C may be deactivating chemicals.

The deactivating chemicals include, but are not limited to, chemicals selected from the group consisting of: hypochlorites, iodophors, quaternary ammonium chlorides (Quats), acid sanitizers, aldehydes (formaldehyde and glutaraldehyde), alcohols, phenolics, peracetic acid (PAA), chlorine dioxide. Specific examples of deactivating chemicals, include, but are not limited to, liquids, such as hydrogen peroxide, peracids such as peracetic acid, and bleach, as well as gases, such as ozone, ammonia, ethylene oxide, fluorine containing chemicals, chlorine containing chemicals, bromine containing chemicals, other highly oxidative gases, and combinations thereof.

Examples of base chemicals, include, but are not limited to, water, de-ionized water, distilled water, an alcohol (e.g., a tertiary alcohol), a glycol-containing chemical compound, and mixtures thereof. Glycol-containing chemical compounds include, but are not limited to, polyethylene glycol, diethylene glycol, triethylene glycol, tetraethylene glycol, glycol ethers, polypropylene glycol, propylene glycol, and combinations thereof. As indicated above, the base chemical may itself be a deactivating chemical. Therefore, the base chemical may also be any one of the deactivating chemicals listed above.

Some typical combinations of a deactivating chemical and a base fluid, include, but are not limited to, hydrogen peroxide and water, bleach and water, peracid and water, peracetic acid and water, alcohol and water, and ozone dissolved in a glycol, an alcohol (e.g., tertiary alcohol), or water.

Other modifications and alterations will occur to others upon their reading and understanding of the specification. It is intended that all such modifications and alterations be included insofar as they come within the scope of the invention as claimed or the equivalents thereof.

Having described the invention, the following is claimed:

1. A method for deactivating a contamination inside a chamber, the method comprising:
combining a plurality of chemical components in the chamber to form a solution, each chemical component having a respective concentration therein, wherein the respective concentrations of the chemical components are determined by:
exposing at least one capacitor, having first and second plates, to the solution, and
determining a change in an electrical property of the at least one capacitor, wherein said change in the electrical property varies in accordance with a change in the respective concentrations of the chemical components in the solution.

2. A method according to claim 1, wherein said method further comprises:
storing a plurality of data sets in a memory, wherein each said data set includes a value indicative of said electrical property as a function of a concentration of at least one of said chemical components.

3. A method according to claim 1, wherein said method further comprises:
maintaining at least one of said plurality of chemical components in the chamber at a respective predetermined concentration.

4. A method according to claim 3, wherein said method further comprises:
selecting at least one contamination to be deactivated in said chamber, wherein said plurality of chemical components, and said respective predetermined concentrations are determined in accordance with the at least one selected contamination.

5. A method according to claim 1, wherein at least one of said plurality of chemical components is a deactivating chemical.

6. A method according to claim 5, wherein said deactivating chemical is selected from the group consisting of: a liquid and an oxidative gas.

7. A method according to claim 5, wherein said deactivating chemical is selected from a group consisting of: hydrogen peroxide, peracid, peracetic acid, bleach, ozone, ammonia, ethylene oxide, fluorine containing chemicals, bromine containing chemicals and chlorine containing chemicals, and combinations thereof.

8. A method according to claim 5, wherein said deactivating chemical is selected from the group consisting of: hypochlorites, iodophors, quanternary ammonium chlorides (Quats), acid sanitizers, aldehydes, alcohols, phenolics, peracetic acid, and chlorine dioxide.

9. A method according to claim 1, wherein at least one of said plurality of chemical components is comprised of a base chemical.

10. A method according to claim 9, wherein said base chemical is at least one of: (a) a diluent for a deactivating chemical, (b) a vehicle for a deactivating chemical, and (c) a deactivating chemical.

11. A method according to claim 9, wherein at least one of said plurality of chemical components is comprised of a base chemical and a deactivating chemical.

12. A method according to claim 9, wherein said base chemical is selected from a group consisting of: water, an alcohol, a glycol-containing chemical compound, and combinations thereof.

13. A method according to claim 12, wherein said glycol-containing chemical compound is selected from a group consisting of: polyethylene glycol, diethylene glycol, triethylene glycol, tetraethylene glycol, glycol ethers, polypropylene glycol, propylene glycol, and combinations thereof.

14. A method according to claim 12, wherein said alcohol is a tertiary alcohol.

15. A method according to claim 1, wherein the method further comprises:
 determining the respective concentration of at least one of said plurality of chemical components by interpolating or extrapolating data from a plurality of data sets stored in a memory, wherein each said data set includes a value indicative of said electrical property as a function of a concentration of at least one of said chemical components.

16. A method according to claim 1, wherein at least one of said plurality of chemical components is a pre-treatment chemical.

17. A method according to claim 1, wherein said method further comprises:
 storing a plurality of data sets in a memory, each data set respectively indicative of decay of a chemical component, wherein each data set includes values of an electrical property of a capacitor associated with chemical component concentrations as a function of time.

18. A method according to claim 17, wherein said method further comprises:
 replenishing the concentration of at least one of said plurality of chemical components in accordance with the plurality of data sets.

19. A method according to claim 18, wherein the concentration of at least one of said plurality of chemical components is replenished when an operating time period elapses.

20. A method according to claim 19, wherein said operating time period is established by at least one of: selecting a predetermined time interval, sensing a change in the electrical property of the capacitor in reference to a threshold value, and sensing a predetermined percentage change in the electrical property of the capacitor.

21. A method according to claim 17, wherein said method further comprises:
 determining a decay rate for each of said plurality of chemical components from said plurality of data sets.

22. A method for deactivating a contamination inside a chamber, the method comprising:
 selecting at least one contamination to be deactivated in the chamber; and
 combining a plurality of chemical components in the chamber to form a solution, each chemical component having a respective concentration therein,
 wherein the concentration of the first and second chemical components are determined by:
  exposing at least one capacitor, having first and second plates, to the solution, and
  determining a change in an electrical property of the at least one capacitor, wherein said change in the electrical property varies in accordance with changes in the respective concentrations of at least one of said chemical components.

23. A method according to claim 22, wherein said method further comprises:
 storing a plurality of data sets in a memory, wherein each said data set includes a value indicative of said electrical property as a function of a concentration of at least one of said chemical components.

24. A method according to claim 22, wherein said method further comprises:
 maintaining at least one of said plurality of chemical components in the chamber at a respective predetermined concentration.

25. A method according to claim 22 wherein at least one of said plurality of chemical components is a deactivating chemical.

26. A method according to claim 25, wherein said deactivating chemical is selected from the group consisting of: a liquid and an oxidative gas.

27. A method according to claim 25, wherein said deactivating chemical is selected from a group consisting of: hydrogen peroxide, peracid, peracetic acid, bleach, ozone, ammonia, ethylene oxide, fluorine containing chemicals, bromine containing chemicals, chlorine containing chemicals, and combinations thereof.

28. A method according to claim 25, wherein said deactivating chemical is selected from the group consisting of: hypochlorites, iodophors, quanternary ammonium chlorides (Quats), acid sanitizers, aldehydes, alcohols, phenolics, peracetic acid, and chlorine dioxide.

29. A method according to claim 22, wherein at least one of said plurality of chemical components is comprised of a base chemical.

30. A method according to claim 29, wherein said base chemical is at least one of: (a) a diluent for a deactivating chemical, (b) a vehicle for a deactivating chemical, and (c) a deactivating chemical.

31. A method according to claim 29, wherein at least one of said plurality of chemical components is comprised of a base chemical and a deactivating chemical.

32. A method according to claim 29, wherein said base chemical is selected from a group consisting of: water, an alcohol, a glycol-containing chemical compound, and combinations thereof.

33. A method according to claim 32, wherein said glycol-containing chemical compound is selected from a group consisting of: polyethylene glycol, diethylene glycol, triethylene glycol, tetraethylene glycol, glycol ethers, polypropylene glycol, propylene glycol, and combinations thereof.

34. A method according to claim 32, wherein said alcohol is a tertiary alcohol.

35. A method according to claim 22, wherein the method further comprises:
 determining the respective concentration of at least one of said plurality of chemical components by interpolating or extrapolating data from a plurality of data sets stored in a memory, wherein each said data set includes a value indicative of said electrical property as a function of a concentration of at least one of said chemical components.

36. A method according to claim 22, wherein at least one of said plurality of chemical components is a pre-treatment chemical.

37. A system for deactivating a contamination inside a chamber, the system comprising:
 means for combining a plurality of chemical components in the chamber to form a solution, each chemical component having a respective concentration therein;

means for determining the respective concentrations of the chemical components including:
  at least one capacitor, having first and second plates exposed to the solution, and
  means for determining a change in an electrical property of the at least one capacitor, wherein said change in the electrical property varies in accordance with a change in the respective concentrations of the chemical components in the solution.

38. A system according to claim 37, wherein said system further comprises:
  storage means for storing a plurality of data sets in a memory, wherein each said data set includes a value indicative of said electrical property as a function of a concentration of at least one of said chemical components.

39. A system according to claim 37, wherein said system further comprises:
  control means for maintaining at least one of said plurality of chemical components in the chamber at a respective predetermined concentration.

40. A system according to claim 37, wherein said system further comprises:
  input means for selecting at least one contamination to be deactivated in said chamber, wherein said plurality of chemical components, and said respective predetermined concentrations are determined in accordance with the at least one selected contamination.

41. A system according to claim 37, wherein at least one of said plurality of chemical components is a deactivating chemical.

42. A system according to claim 41, wherein said deactivating chemical is selected from the group consisting of a liquid and an oxidative gas.

43. A system according to claim 41, wherein said deactivating chemical is selected from a group consisting of hydrogen peroxide, peracid, peracetic acid, bleach, ozone, ammonia, ethylene oxide, fluorine containing chemicals, bromine containing chemicals, and chlorine containing chemicals and combinations thereof.

44. A system according to claim 41, wherein said deactivating chemical is selected from the group consisting of: hypochlorites, iodophors, quanternary ammonium chlorides (Quats), acid sanitizers, aldehydes, alcohols, phenolics, peracetic acid, and chlorine dioxide.

45. A system according to claim 41, wherein at least one of said plurality of chemical components is comprised of a base chemical.

46. A system according to claim 45, wherein said base chemical is at least one of: (a) a diluent for a deactivating chemical, (b) a vehicle for a deactivating chemical, and (c) a deactivating chemical.

47. A system according to claim 45, wherein at lease one of said plurality of chemical components is comprised of a base chemical and a deactivating chemical.

48. A system according to claim 45, wherein said base chemical is selected from a group consisting of: water, an alcohol, a glycol-containing chemical compound, and combinations thereof.

49. A system according to claim 48, wherein said glycol-containing chemical compound is selected from a group consisting of polyethylene glycol, diethylene glycol, triethylene glycol, tetraethylene glycol, glycol ethers, polypropylene glycol, propylene glycol, and combinations thereof.

50. A system according to claim 48, wherein said alcohol is a tertiary alcohol.

51. A system according to claim 37, wherein said sensor means determines the respective concentration of at least one of said plurality of chemical components by interpolating or extrapolating data from a plurality of data sets stored in a memory, wherein each said data set includes a value indicative of said electrical property as a function of a concentration of at least one of said chemical components.

52. A system according to claim 37, wherein at least one of said plurality of chemical components is a pre-treatment chemical.

53. A system according to claim 37 wherein said system further comprises:
  means for storing a plurality of data sets in a memory, each data set respectively indicative of decay of a chemical component, wherein each data set includes values of an electrical property of a capacitor associated with chemical component concentrations as a function of time.

54. A system according to claim 53, wherein said system further comprises:
  means for replenishing the concentration of at least one of said plurality of chemical components in accordance with the plurality of data sets.

55. A system according to claim 54, wherein the concentration of at least one of said plurality of chemical components is replenished when an operating time period elapses.

56. A system according to claim 55, wherein said operating time period is established by at least one of: selecting a predetermined time interval, sensing a change in the electrical property of the capacitor in reference to a threshold value, and sensing a predetermined percentage change in the electrical property of the capacitor.

57. A system according to claim 53, wherein said system further comprises:
  means for determining a decay rate for at least one of said chemical components from said plurality of data sets.

58. A system according to claim 37, wherein said system further comprises a second capacitor having first and second plates, wherein the second capacitor is exposed to the solution, said second capacitor connected in parallel with a first capacitor.

59. A system for deactivating a contamination inside a chamber, the system comprising:
  input means for selecting at least one contamination to be deactivated in the chamber,
  means for combining a plurality of chemical components in the chamber to form a solution, each chemical component having a respective concentration therein; and
  means for determining the respective concentrations of the chemical components including:
    at least one capacitor, having first and second plates exposed to the solution, and
    means for determining a change in an electrical property of the at least one capacitor, wherein said change in the electrical property varies in accordance with a change in the respective concentrations of the chemical components in the solution.

60. A system according to claim 59, wherein said system further comprises:
  storage means for storing a plurality of data sets in a memory, wherein each said data set includes a value indicative of said electrical property as a function of a concentration of at least one of said chemical components.

61. A system according to claim 59, wherein said system further comprises:
  control means for maintaining at least one of said plurality of chemical components in the chamber at a respective predetermined concentration.

62. A system according to claim 59, wherein said at least one of said plurality of chemical components is a deactivating chemical.

63. A system according to claim 62, wherein said deactivating chemical is selected from the group consisting of a liquid and an oxidative gas.

64. A system according to claim 62, wherein said deactivating chemical is selected from a group consisting of hydrogen peroxide, peracid, peracetic acid, bleach, ozone, ammonia, ethylene oxide, fluorine containing chemicals, and chlorine containing chemicals.

65. A system according to claim 62, wherein said deactivating chemical is selected from the group consisting of: hypochlorites, iodophors, quanternary ammonium chlorides (Quats), acid sanitizers, aldehydes, alcohols, phenolics, peracetic acid, and chlorine dioxide.

66. A system according to claim 62, wherein at least one of said plurality of chemical components is comprised of a base chemical.

67. A system according to claim 66, wherein said base chemical is at least one of: (a) a diluent for a deactivating chemical, (b) a vehicle for a deactivating chemical, and (c) a deactivating chemical.

68. A system according to claim 66, wherein at least one of said plurality of chemical components is comprised of a base chemical and a deactivating chemical.

69. A system according to claim 66, wherein said base chemical is selected from a group consisting of: water, an alcohol, a glycol-containing chemical compound, and combinations thereof.

70. A system according to claim 69, wherein said glycol-containing chemical compound is selected from a group consisting of polyethylene glycol, diethylene glycol, triethylene glycol, tetraethylene glycol, glycol ethers, polypropylene glycol, propylene glycol, and combinations thereof.

71. A system according to claim 59, wherein said sensor means determines the respective concentration of at least one of said plurality of chemical components by interpolating or extrapolating data from a plurality of data sets stored in a memory, wherein each said data set includes a value indicative of said electrical property as a function of a concentration of at least one of said chemical components.

72. A system according to claim 59, wherein said system further comprises:

means for determining a decay rate for each of at least one of said chemical components from said plurality of data sets.

73. A system according to claim 59, wherein said system further comprises a second capacitor having first and second plates, wherein the second capacitor is exposed to the solution, said second capacitor connected in parallel with a first capacitor.

74. A method of controlling the concentration of a plurality of chemical components of a solution in a chamber, the method comprising:

storing a plurality of data sets in a memory, each data set respectively indicative of decay of a chemical component, wherein each data set includes values of an electrical property of a capacitor associated with chemical component concentrations as a function of time; and replenishing the concentration of at least one of the chemical components after an operating time period in accordance with the plurality of data sets.

75. A method according to claim 74, wherein said operating time period is established by at least one of: selecting a predetermined time interval, sensing a change in the electrical property of the capacitor in reference to a threshold value, and sensing a predetermined percentage change in the electrical property of the capacitor.

76. A method of controlling concentration of a chemical component of a solution in a chamber, the method comprising:

developing an equation defining an electrical property of a capacitor associated with concentration of a chemical component as a function of time; and replenishing the concentration of the chemical component after an operating time period in accordance with said equation.

* * * * *